United States Patent
Sun et al.

(10) Patent No.: US 9,567,574 B2
(45) Date of Patent: Feb. 14, 2017

(54) POLYPEPTIDES HAVING GLUCOAMYLASE ACTIVITY AND POLYNUCLEOTIDES ENCODING SAME

(75) Inventors: Tianqi Sun, Beijing (CN); Ming Li, Beijing (CN)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 14/343,911

(22) PCT Filed: Sep. 7, 2012

(86) PCT No.: PCT/CN2012/081124
§ 371 (c)(1),
(2), (4) Date: Jun. 27, 2014

(87) PCT Pub. No.: WO2013/034097
PCT Pub. Date: Mar. 14, 2013

(65) Prior Publication Data
US 2014/0308725 A1  Oct. 16, 2014

Related U.S. Application Data

(60) Provisional application No. 61/538,995, filed on Sep. 26, 2011.

(30) Foreign Application Priority Data

Sep. 9, 2011 (WO) ................ PCT/CN2011/079528

(51) Int. Cl.
| | |
|---|---|
| C12N 9/24 | (2006.01) |
| C12P 7/14 | (2006.01) |
| C12P 19/02 | (2006.01) |
| C12P 19/14 | (2006.01) |
| C12N 9/34 | (2006.01) |
| C13K 1/06 | (2006.01) |

(52) U.S. Cl.
CPC ............. *C12N 9/2428* (2013.01); *C12P 7/14* (2013.01); *C12P 19/02* (2013.01); *C12P 19/14* (2013.01); *C12Y 302/01003* (2013.01); *C13K 1/06* (2013.01); *C12P 2203/00* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 5,665,585 A * | 9/1997 | Torkkeli et al. | ............. 435/203 |
| 2005/0176120 A1 * | 8/2005 | Otto | .......... C12R 1/07 |
| | | | 435/139 |
| 2008/0090271 A1 | 4/2008 | Udagawa | |

FOREIGN PATENT DOCUMENTS

| | | |
|---|---|---|
| WO | 99/28448 A1 | 6/1999 |
| WO | 2005/045018 A1 | 5/2005 |
| WO | 2007/057018 A2 | 5/2007 |

OTHER PUBLICATIONS

Amlacher et al, 2011, Cell 146, 277-289.
Amlacher, NCBI 2011—Seq No. EGS 22528.
Amlacher, NCBI 2011—Seq No. EGS 23530.
Chen et al, 2007, J Appl Microbiol 103 (6), 2277-2284.

* cited by examiner

*Primary Examiner* — Suzanne M Noakes
(74) *Attorney, Agent, or Firm* — David Fazzolare

(57) ABSTRACT

The present invention provides isolated polypeptides having glucoamylase activity, catalytic domains, and polynucleotides encoding the polypeptides, catalytic domains. The invention also provides nucleic acid constructs, vectors and host cells comprising the polynucleotides as well as methods of producing and using the polypeptides, catalytic domains.

24 Claims, No Drawings

POLYPEPTIDES HAVING GLUCOAMYLASE ACTIVITY AND POLYNUCLEOTIDES ENCODING SAME

CROSS-REFERENCE TO RELATED APPLICATIONS

This application is a 35 U.S.C. 371 national application of PCT/CN2012/081124 filed Sep. 7, 2012, which claims priority or the benefit under 35 U.S.C. 119 of International application no. PCT/CN11/079528 filed Sep. 9, 2011 and U.S. provisional application No. 61/538,995 filed Sep. 26, 2011, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having glucoamylase activity and polynucleotides encoding the polypeptides. The invention also relates to nucleic acid constructs, vectors, and host cells comprising the polynucleotides as well as methods for producing and using the polypeptides, and to the use of glucoamylases of the invention for starch conversion to producing fermentation products, such as ethanol, and syrups, such as glucose. The invention also relates to a composition comprising a glucoamylase of the invention.

Description of the Related Art

Glucoamylase (1,4-alpha-D-glucan glucohydrolase, EC 3.2.1.3) is an enzyme, which catalyzes the release of D-glucose from the non-reducing ends of starch or related oligo- and polysaccharide molecules. Glucoamylases are produced by several filamentous fungi and yeast, with those from *Aspergillus* being commercially most important.

Commercially, glucoamylases are used to convert starchy material, which is already partially hydrolyzed by an alpha-amylase, to glucose. The glucose may then be converted directly or indirectly into a fermentation product using a fermenting organism. Examples of commercial fermentation products include alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); hormones, and other compounds which are difficult to produce synthetically. Fermentation processes are also commonly used in the consumable alcohol (e.g., beer and wine), dairy (e.g., in the production of yogurt and cheese) industries.

The end product may also be syrup. For instance, the end product may be glucose, but may also be converted, e.g., by glucose isomerase to fructose or a mixture composed almost equally of glucose and fructose. This mixture, or a mixture further enriched with fructose, is the most commonly used high fructose corn syrup (HFCS) commercialized throughout the world. Amlacher et al., 2011 (Cell 146, 277-289) reports the genome of *Chaetomium thermophilum*. It is an object of the present invention to provide polypeptides having glucoamylase activity and polynucleotides encoding the polypeptides and which provide a high yield in fermentation product production processes, such as ethanol production processes, including one-step ethanol fermentation processes from un-gelatinized raw (or uncooked) starch.

SUMMARY OF THE INVENTION

Polypeptides produced by the fungus *Chaetomium* and having glucoamylase activity have been identified and characterized. More particularly the *Chaetomium* sp. is selected from *Chaetomium thermophilum*.

The present invention relates to isolated polypeptides having glucoamylase activity, selected from the group consisting of:

(a) a polypeptide having at least 76% sequence identity to the mature polypeptide of SEQ ID NO: 2 or SEQ ID NO: 4;

(b) a polypeptide encoded by a polynucleotide that hybridizes under medium stringency conditions with (i) the mature polypeptide coding sequence of SEQ ID NO: 1 or SEQ ID NO: 3, (ii) the cDNA sequence thereof, or (iii) the full-length complement of (i) or (ii);

(c) a polypeptide encoded by a polynucleotide having at least 76% sequence identity to the mature polypeptide coding sequence of SEQ ID NO: 1 or SEQ ID NO: 3, or the cDNA sequence thereof;

(d) a variant of the mature polypeptide of SEQ ID NO: 2 or SEQ ID NO: 4 comprising a substitution, deletion, and/or insertion at one or more positions; and (e) a fragment of the polypeptides of (a), (b), (c), or (d) that has glucoamylase activity.

The present invention also relates to isolated polypeptides comprising a catalytic domain selected from the group consisting of:

(a) a catalytic domain having at least 76% sequence identity to amino acids 33 to 505 of SEQ ID NO: 2 or amino acids 28 to 504 of SEQ ID NO: 4;

(b) a catalytic domain encoded by a polynucleotide that hybridizes under medium stringency conditions with (i) nucleotides 97 to 1609 of SEQ ID NO: 1 or nucleotides 82 to 1680 of SEQ ID NO: 3, (ii) the cDNA sequence thereof, or (iii) the full-length complement of (i) or (ii);

(c) a catalytic domain encoded by a polynucleotide having at least 76% sequence identity to nucleotides 97 to 1609 of SEQ ID NO: 1 or nucleotides 82 to 1680 of SEQ ID NO: 3 or the cDNA sequences thereof;

(d) a variant of amino acids 33 to 505 of SEQ ID NO: 2 or amino acids 28 to 504 of SEQ ID NO: 4 comprising a substitution, deletion, and/or insertion at one or more (e.g., several) positions; and (e) a fragment of the catalytic domain of (a), (b), (c), or (d) that has glucoamylase activity.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to methods of producing a fermentation product from starch containing material and to compositions comprising the glucoamylase of the invention.

DEFINITIONS

Glucoamylase: The term glucoamylase (1,4-alpha-D-glucan glucohydrolase, EC 3.2.1.3) is defined as an enzyme, which catalyzes the release of D-glucose from the non-reducing ends of starch or related oligo- and polysaccharide molecules. For purposes of the present invention, glucoamylase activity is determined according to the procedure described in the 'Materials & Methods'-section herein.

The polypeptides of the present invention have at least 20%, preferably at least 40%, preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 100% of the glucoamylase activity of the mature polypeptide of SEQ ID NO: 2 or at least 20%, preferably at least 40%, preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 100% of the glucoamylase activity of the mature polypeptide of SEQ ID NO: 4.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Binding domain: The term "carbohydrate binding domain" means the region of an enzyme that mediates binding of the enzyme to the carbohydrate substrate. The carbohydrate binding domain (CBD) is typically found either at the N-terminal or at the C-terminal extremity of an glucoamylase. The CBD is also sometimes referred to as a starch binding domain, SBD. In one embodiment the CBD is amino acids 526 to 634 of SEQ ID NO: 2 or amino acids 510 to 631 of SEQ ID NO: 4.

Catalytic domain: The term "catalytic domain" means the region of an enzyme containing the catalytic machinery of the enzyme. In one embodiment the catalytic domain is amino acids 33 to 505 of SEQ ID NO: 2 or amino acids 28 to 504 of SEQ ID NO: 4.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic domain having one or more (e.g., several) amino acids absent from the amino and/or carboxyl terminus of a mature polypeptide or domain; wherein the fragment has glucoamylase activity. In one aspect, a fragment contains at least 473-amino acid residues (e.g., amino acids 33 to 505 of SEQ ID NO: 2), or at least 477-amino acid residues (e.g., amino acids 28 to 504 of SEQ ID NO: 4).

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 20 to 634 of SEQ ID NO: 2 based on the SignalP program (Nielsen et al., 1997, *Protein Engineering* 10:1-6) that predicts amino acids 1 to 19 of SEQ ID NO: 2 are a signal peptide. In another aspect, the mature polypeptide is amino acids 20 to 631 of SEQ ID NO: 4 based on the SignalP program (Nielsen et al., 1997, *Protein Engineering* 10:1-6) that predicts amino acids 1 to 19 of SEQ ID NO: 4 are a signal peptide.

It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having glucoamylase activity. In one aspect, the mature polypeptide coding sequence is nucleotides 58 to 1999 (including the stop codon) of SEQ ID NO: 1 or the cDNA sequence thereof based on the SignalP (Nielsen et al., 1997, supra) that predicts nucleotides 1 to 57 of SEQ ID NO: 1 encode a signal peptide. In another aspect the mature polypeptide coding sequence is nucleotides 58-241, and 336-1996 of SEQ ID NO 1.

In another aspect, the mature polypeptide coding sequence is nucleotides 58 to 2064 (including the stop codon) of SEQ ID NO: 3 or the cDNA sequence thereof based on the SignalP (Nielsen et al., 1997, supra) that predicts nucleotides 1 to 57 of SEQ ID NO: 3 encode a signal peptide. In another aspect the mature polypeptide coding sequence is nucleotides 58-103, 160-273, 332-701, and 756-2061 of SEQ ID NO 3.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM 62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment—
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment—Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having glucoamylase activity. In one aspect, a subsequence contains at least 1419 nucleic acid residues (e.g., nucleotides 97 to 241, 336 to 1609 of SEQ ID NO: 1), or at least 1431 nucleic acid residues (e.g., nucleotides 82 to 103, 160 to 273, 332 to 701, 756 to 1680 of SEQ ID NO: 3).

Variant: The term "variant" means a polypeptide having glucoamylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

DETAILED DESCRIPTION OF THE INVENTION

Polypeptides Having Glucoamylase Activity

In an embodiment, the present invention relates to isolated polypeptides having a sequence identity to the mature polypeptide of SEQ ID NO: 2 of at least 76%, at least 78%, at least 80%, at least 85%, at least 90%, at least 91%, at least 92%, at least 93%, at least 94%, at least 95%, at least 96%, at least 97%, at least 98%, at least 99%, or 100%, which have glucoamylase activity. In one aspect, the polypeptides differ by no more than 10 amino acids, e.g., 1, 2, 3, 4, 5, 6, 7, 8, or 9, from the mature polypeptide of SEQ ID NO: 2.

A polypeptide of the present invention preferably comprises or consists of the amino acid sequence of SEQ ID NO: 2 or an allelic variant thereof; or is a fragment thereof having glucoamylase activity. In another aspect, the polypeptide comprises or consists of the mature polypeptide of SEQ ID NO: 2. In another aspect, the polypeptide comprises or consists of amino acids 20 to 634 of SEQ ID NO: 2.

In an embodiment, the present invention relates to isolated polypeptides having a sequence identity to the mature polypeptide of SEQ ID NO: 4 of at least 76%, at least 78%, at least 80%, at least 85%, at least 90%, at least 91%, at least 92%, at least 93%, at least 94%, at least 95%, at least 96%, at least 97%, at least 98%, at least 99%, or 100%, which have glucoamylase activity. In one aspect, the polypeptides differ by no more than 10 amino acids, e.g., 1, 2, 3, 4, 5, 6, 7, 8, or 9, from the mature polypeptide of SEQ ID NO: 4.

A polypeptide of the present invention preferably comprises or consists of the amino acid sequence of SEQ ID NO: 4 or an allelic variant thereof; or is a fragment thereof having glucoamylase activity. In another aspect, the polypeptide comprises or consists of the mature polypeptide of SEQ ID NO: 4. In another aspect, the polypeptide comprises or consists of amino acids 20 to 631 of SEQ ID NO: 4.

In another embodiment, the present invention relates to an isolated polypeptide having glucoamylase activity encoded by a polynucleotide that hybridizes under medium, medium-high stringency conditions, high stringency conditions, or very high stringency conditions with (i) the mature polypeptide coding sequence of SEQ ID NO: 1, (ii) the cDNA sequence thereof, or (iii) the full-length complement of (i) or (ii) (Sambrook et al., 1989, *Molecular Cloning, A Laboratory Manual*, 2d edition, Cold Spring Harbor, N.Y.).

In another embodiment, the present invention relates to an isolated polypeptide having glucoamylase activity encoded by a polynucleotide that hybridizes under medium, medium-high stringency conditions, high stringency conditions, or very high stringency conditions with (i) the mature polypeptide coding sequence of SEQ ID NO: 3, (ii) the cDNA sequence thereof, or (iii) the full-length complement of (i) or (ii) (Sambrook et al., 1989, *Molecular Cloning, A Laboratory Manual*, 2d edition, Cold Spring Harbor, N.Y.).

The polynucleotide of SEQ ID NO: 1 or SEQ ID NO: 3, or a subsequence thereof, as well as the polypeptide of SEQ ID NO: 2 or SEQ ID NO: 4, or a fragment thereof, may be used to design nucleic acid probes to identify and clone DNA encoding polypeptides having glucoamylase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length.

Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having glucoamylase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1 or SEQ ID NO: 3; (ii) the mature polypeptide coding sequence of SEQ ID NO: 1 or SEQ ID NO: 3; (iii) the cDNA sequences thereof; (iv) the full-length complement thereof; or (v) a subsequence thereof; under medium to very high stringency conditions. Molecules to which the nucleic acid probe hybridizes under these conditions can be detected using, for example, X-ray film or any other detection means known in the art.

In one aspect, the nucleic acid probe is nucleotides 58-241, and 336-1996 of SEQ ID NO 1. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1 or the cDNA sequence thereof.

In one aspect, the nucleic acid probe is nucleotides 58-103, 160-273, 332-701, and 756-2061 of SEQ ID NO 3. In another aspect, the nucleic acid probe is a polynucleotide that encodes the polypeptide of SEQ ID NO: 4; the mature polypeptide thereof; or a fragment thereof. In another aspect, the nucleic acid probe is SEQ ID NO: 3 or the cDNA sequence thereof.

In another embodiment, the present invention relates to an isolated polypeptide having glucoamylase activity encoded by a polynucleotide having a sequence identity to the mature polypeptide coding sequence of SEQ ID NO: 1 or the cDNA sequence thereof of at least 76%, at least 78%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to an isolated polypeptide having glucoamylase activity encoded by a polynucleotide having a sequence identity to the mature polypeptide coding sequence of SEQ ID NO: 3 or the cDNA sequence thereof of at least 76%, at least 78%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2 or SEQ ID NO: 4 comprising a substitution, deletion, and/or insertion at one or more (e.g., several) positions. In an embodiment, the number of amino acid substitutions, deletions and/or insertions introduced into the mature polypeptide of SEQ ID NO: 2 or SEQ ID NO: 4 is not more than 10, e.g., 1, 2, 3, 4, 5, 6, 7, 8 or 9. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for glucoamylase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al, 2000, J. Biotechnol. 76: 245-251; Rasmussen-Wilson et al, 1997, Appl. Environ. Microbiol. 63: 3488-3493; Ward et al, 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

Sources of Polypeptides Having Glucoamylase Activity

A polypeptide having glucoamylase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. For example, the polypeptide may be a *Chaetomium* polypeptide.

In another aspect, the polypeptide is a *Chaetomium thermophilum* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

In one embodiment, the present invention also relates to catalytic domains having a sequence identity to amino acids 33 to 505 of SEQ ID NO: 2 of at least 76%, at least 78%, at least 80%, at least 85%, at least 90%, at least 95%, at least 96%, at least 97%, at least 98%, at least 99%, or 100%. In one aspect, the catalytic domains comprise amino acid sequences that differ by no more than 10 amino acids, e.g., 1, 2, 3, 4, 5, 6, 7, 8, or 9, from amino acids 33 to 505 of SEQ ID NO: 2.

The catalytic domain preferably comprises or consists of amino acids 33 to 505 of SEQ ID NO: 2 or an allelic variant thereof; or is a fragment thereof having glucoamylase activity.

In another embodiment, the present invention also relates to catalytic domains encoded by polynucleotides that hybridize under medium stringency conditions, medium-high stringency conditions, high stringency conditions, or very high stringency conditions (as defined above) with (i) the nucleotides 97 to 1624 of SEQ ID NO: 1, (ii) the cDNA sequence thereof, or (iii) the full-length complement of (i) or (ii) (Sambrook et al., 1989, supra).

In another embodiment, the present invention also relates to catalytic domains encoded by polynucleotides having a sequence identity to nucleotides 97 to 1609 of SEQ ID NO: 1 or the cDNA sequence thereof of at least 76%, at least 78%, at least 80%, at least 85%, at least 90%, at least 95%, at least 96%, at least 97%, at least 98%, at least 99%, or 100%.

The polynucleotide encoding the catalytic domain preferably comprises or consists of nucleotides 97 to 1609 of SEQ ID NO: 1 In another embodiment, the present invention also relates to catalytic domain variants of amino acids 33 to 505 of SEQ ID NO: 2 comprising a substitution, deletion, and/or insertion at one or more (e.g., several) positions. In one aspect, the number of amino acid substitutions, deletions and/or insertions introduced into the sequence of amino acids 33 to 505 of SEQ ID NO: 2 is 10, e.g., 1, 2, 3, 4, 5, 6, 8, or 9.

In another embodiment, the present invention also relates to catalytic domains having a sequence identity to amino acids 28 to 504 of SEQ ID NO: 4 of at least 76%, at least 78%, at least 80%, at least 85%, at least 90%, at least 95%, at least 96%, at least 97%, at least 98%, at least 99%, or 100%. In one aspect, the catalytic domains comprise amino acid sequences that differ by no more than 10 amino acids, e.g., 1, 2, 3, 4, 5, 6, 7, 8, or 9, from amino acids 28 to 504 of SEQ ID NO: 4.

The catalytic domain preferably comprises or consists of amino acids 28 to 504 of SEQ ID NO: 4 or an allelic variant thereof; or is a fragment thereof having glucoamylase activity.

In another embodiment, the present invention also relates to catalytic domains encoded by polynucleotides that hybridize under medium stringency conditions, medium-high stringency conditions, high stringency conditions, or very high stringency conditions (as defined above) with (i) the nucleotides 82 to 1680 of SEQ ID NO: 3, (ii) the cDNA sequence thereof, or (iii) the full-length complement of (i) or (ii) (Sambrook et al., 1989, supra).

In another embodiment, the present invention also relates to catalytic domains encoded by polynucleotides having a sequence identity to nucleotides 82 to 1680 of SEQ ID NO: 3 or the cDNA sequence thereof of at least 76%, at least 78%, at least 80%, at least 85%, at least 90%, at least 95%, at least 96%, at least 97%, at least 98%, at least 99%, or 100%.

The polynucleotide encoding the catalytic domain preferably comprises or consists of nucleotides 82 to 1680 of SEQ ID NO: 3 In another embodiment, the present invention also relates to catalytic domain variants of amino acids 28 to 504 of SEQ ID NO: 4 comprising a substitution, deletion, and/or insertion at one or more (e.g., several) positions. In one aspect, the number of amino acid substitutions, deletions and/or insertions introduced into the sequence of amino acids 31 to 430 of SEQ ID NO: 4 is 10, e.g., 1, 2, 3, 4, 5, 6, 8, or 9.

The catalytic domain according to the invention may in one embodiment further comprise a carbohydrate binding domain.

Binding Domains

In one embodiment, the present invention also relates to carbohydrate binding domains having a sequence identity to amino acids 526 to 634 of SEQ ID NO: 2 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one aspect, the carbohydrate binding domains comprise amino acid sequences that differ by no more than 10 amino acids, e.g., 1, 2, 3, 4, 5, 6, 7, 8, or 9, from amino acids 526 to 634 of SEQ ID NO: 2.

The carbohydrate binding domain preferably comprises or consists of amino acids 526 to 634 of SEQ ID NO: 2 or an allelic variant thereof; or is a fragment thereof having carbohydrate binding activity.

In another embodiment, the present invention also relates to carbohydrate binding domains encoded by polynucleotides that hybridize under very low stringency conditions, low stringency conditions, medium stringency conditions, medium-high stringency conditions, high stringency conditions, or very high stringency conditions (as defined above) with (i) the nucleotides 1670 to 1996 of SEQ ID NO: 1, or (ii) the full-length complement of (i) (Sambrook et al., 1989, supra).

In another embodiment, the present invention also relates to carbohydrate binding domains encoded by polynucleotides having a sequence identity to nucleotides 1670 to 1996 of SEQ ID NO: 1 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The polynucleotide encoding the carbohydrate binding domain preferably comprises or consists of nucleotides 1670 to 1996 of SEQ ID NO: 1.

In another embodiment, the present invention also relates to carbohydrate binding domain variants of amino acids 526 to 634 of SEQ ID NO: 2 comprising a substitution, deletion, and/or insertion at one or more (e.g., several) positions. In one aspect, the number of amino acid substitutions, deletions and/or insertions introduced into the sequence of amino acids 526 to 634 of SEQ ID NO: 2 is 10, e.g., 1, 2, 3, 4, 5, 6, 8, or 9.

In another embodiment, the present invention also relates to carbohydrate binding domains having a sequence identity to amino acids 510 to 631 of SEQ ID NO: 4 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one aspect, the carbohydrate binding domains comprise amino acid sequences that differ by no more than 10 amino acids, e.g., 1, 2, 3, 4, 5, 6, 7, 8, or 9, from amino acids 510 to 631 of SEQ ID NO: 4.

The carbohydrate binding domain preferably comprises or consists of amino acids 510 to 631 of SEQ ID NO: 4 or an allelic variant thereof; or is a fragment thereof having carbohydrate binding activity.

In another embodiment, the present invention also relates to carbohydrate binding domains encoded by polynucleotides that hybridize under very low stringency conditions, low stringency conditions, medium stringency conditions, medium-high stringency conditions, high stringency conditions, or very high stringency conditions (as defined above) with (i) the nucleotides 1696 to 2061 of SEQ ID NO: 3, or (ii) the full-length complement of (i) (Sambrook et al., 1989, supra).

In another embodiment, the present invention also relates to carbohydrate binding domains encoded by polynucleotides having a sequence identity to nucleotides 1696 to 2061 of SEQ ID NO: 3 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The polynucleotide encoding the carbohydrate binding domain preferably comprises or consists of nucleotides 1696 to 2061 of SEQ ID NO: 3.

In another embodiment, the present invention also relates to carbohydrate binding domain variants of amino acids 510 to 631 of SEQ ID NO: 4 comprising a substitution, deletion, and/or insertion at one or more (e.g., several) positions. In one aspect, the number of amino acid substitutions, deletions and/or insertions introduced into the sequence of amino acids 510 to 631 of SEQ ID NO: 4 is 10, e.g., 1, 2, 3, 4, 5, 6, 8, or 9.

A catalytic domain operably linked to the carbohydrate binding domain of the invention may be from a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase. In one particular embodiment the catalytic domain is from a glucoamylase. In another particular embodiment the catalytic domain is from an amylase. The polynucleotide encoding the catalytic domain may be obtained from any prokaryotic, eukaryotic, or other source.

Hybrid Enzymes

The present invention also relates to hybrid enzymes comprising a catalytic domain having enzyme activity (e.g., starch degrading enzyme activity, such as alpha-amylase, amylopullulanase, beta-amylase, CGTase, glucoamylase, isoamylase, maltogenic amylase, or pullulanase activity), and a carbohydrate-binding domain (CBD). The hybrid enzyme may further comprise a linker. In one embodiment the catalytic domain is a catalytic domain according to the invention. In another embodiment the CBD is a CBD according to the invention.

The hybrid may be produced by fusing a first DNA sequence encoding a catalytic domain and a second DNA sequence encoding a carbohydrate-binding module, or the hybrid may be produced as a completely synthetic gene based on knowledge of the amino acid sequences of suitable CBDs, linkers and catalytic domains.

The term "hybrid enzyme" (also referred to as "fusion protein", "hybrid", hybrid polypeptide" or "hybrid protein") is used herein to characterize the hybrid polypeptides of the invention comprising a catalytic module having enzyme activity (e.g., starch degrading enzyme activity, such as alpha-amylase, amylopullulanase, beta-amylase, CGTase, glucoamylase, isoamylase, maltogenic amylase, or pullulanase activity) and a carbohydrate-binding module wherein the catalytic domain and the carbohydrate-binding module are derived from different sources. The term "source" includes, but is not limited to, a parent enzyme or a variant thereof, e.g., an amylase or glucoamylase, or other catalytic activity comprising a suitable catalytic module and/or a suitable CBD and/or a suitable linker. However the CBD may also be derived from a polypeptide having no catalytic activity. The catalytic domain and the carbohydrate binding module may be derived from the same microbial strain, from strains within the same species, from closely related species or less related organisms. Preferably the catalytic domain and the carbohydrate binding module of the hybrids are derived from different sources, e.g., from different enzymes from the same strain and/or species, or e.g., from strains within different species.

Polynucleotides

The present invention also relates to isolated polynucleotides encoding a polypeptide, a catalytic domain, or carbohydrate binding domain of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al, 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Chaetomium*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1 or SEQ ID NO: 3, or the cDNA sequences thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al, 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reeseixylanase* I, *Trichoderma reeseixylanase* II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al, 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al, 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus otyzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al, 1991, *Gene* 98: 61-67; Cullen et al, 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al, 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al, 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (*Praha*) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycotaas well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces,* or *Yarrowia* cell, such as a *Kluyveromyceslactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowialipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinuscinereus, Coriolushirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete Chrysosporium, Phlebiaradiata, Pleurotusetyngii, Thielavia terrestris, Trametesvillosa, Trametesversicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al, 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bactetiol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is a *Chaetomium* cell. In a more preferred aspect, the cell is a *Chaetomium thermophilum* cell.

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al, 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al, 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38)

and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al, 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Compositions

The present invention also relates to compositions comprising a polypeptide of the present invention. Preferably, the compositions are enriched in such a polypeptide. The term "enriched" indicates that the glucoamylase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus, Aspergillus awamori, Aspergillus fumigatus, Aspergillus foetidus, Aspergillus japonicus, Aspergillus nidulans, Aspergillus niger,* or *Aspergillus oryzae; Fusarium,* preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseurn, Fusarium trichothecioides,* or *Fusarium venenatum; Humicola,* preferably *Humicola insolens* or *Humicola lanuginosa;* or *Trichoderma,* preferably *Trichoderma harzianum, Trichoderma koningii, Trichoderma longibrachiatum, Trichoderma reesei,* or *Trichoderma viride.*

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Combination of Glucoamylase and Acid Alpha-Amylase

According to this aspect of the invention a glucoamylase of the invention may be combined with an alpha-amylase, preferably acid alpha-amylase in a ratio of between 0.3 and 5.0 AFAU/AGU. More preferably the ratio between acid alpha-amylase activity and glucoamylase activity is at least 0.35, at least 0.40, at least 0.50, at least 0.60, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.85, or even at least 1.9 AFAU/AGU. However, the ratio between acid alpha-amylase activity and glucoamylase activity should preferably be less than 4.5, less than 4.0, less than 3.5, less than 3.0, less than 2.5, or even less than 2.25 AFAU/AGU. In AUU/AGI the activities of acid alpha-amylase and glucoamylase are preferably present in a ratio of between 0.4 and 6.5 AUU/AGI. More preferably the ratio between acid alpha-amylase activity and glucoamylase activity is at least 0.45, at least 0.50, at least 0.60, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4, or even at least 2.5 AUU/AGI. However, the ratio between acid alpha-amylase activity and glucoamylase activity is preferably less than 6.0, less than 5.5, less than 4.5, less than 4.0, less than 3.5, or even less than 3.0 AUU/AGI.

Above composition is suitable for use in a starch conversion process mentioned below for producing syrup and fermentation products, such as ethanol.

Examples are given below of preferred uses of the polypeptide compositions of the invention. The dosage of the polypeptide composition of the invention and other conditions under which the composition is used may be determined on the basis of methods known in the art.

Uses

The present invention is also directed to processes/methods for using the polypeptides having glucoamylase activity of the invention.

Uses according to the invention include starch conversion of starch to, e.g., syrup and fermentation products, including ethanol and beverages. Examples of processes where a glucoamylase of the invention may be used include the ones described in WO 92/20777, WO 03/066816, WO 03/066826, WO 2004/080923, and WO 2004/081193, which are hereby all incorporated by reference.

Production of Fermentation Products

Process for Producing Fermentation Products from Gelatinized Starch Containing Material In this aspect the present invention relates to a process for producing a fermentation product, especially ethanol, from starch-containing material, which process includes a liquefaction step and sequentially or simultaneously performed saccharification and fermentation steps.

The invention relates to a process for producing a fermentation product from starch-containing material comprising the steps of:

(a) liquefying starch-containing material; preferably using an alpha-amylase (b) saccharifying the liquefied material obtained in step (a) using a glucoamylase of the invention; and (c) fermenting the saccharified material using a fermenting organism.

The fermentation product, such as especially ethanol, may optionally be recovered after fermentation, e.g., by distillation. Suitable starch-containing starting materials are listed in the section "Starch-containing materials"-section below. Contemplated enzymes are listed in the "Enzymes"-section below. The liquefaction is preferably carried out in the presence of an alpha-amylase. The fermentation is preferably carried out in the presence of yeast, preferably a strain of *Saccharomyces*. Suitable fermenting organisms are listed in the "Fermenting Organisms"—section below. In preferred embodiments step (b) and (c) are carried out sequentially or simultaneously (i.e., as SSF process).

In a particular embodiment, the process of the invention further comprises, prior to the step (a), the steps of:

x) reducing the particle size of the starch-containing material, preferably by milling; and y) forming a slurry comprising the starch-containing material and water.

The aqueous slurry may contain from 10-40 wt. %, preferably 25-35 wt. % starch-containing material. The slurry is heated to above the gelatinization temperature and alpha-amylase, preferably bacterial and/or acid fungal alpha-amylase, may be added to initiate liquefaction (thinning). The slurry may in an embodiment be jet-cooked to further gelatinize the slurry before being subjected to an alpha-amylase in step (a) of the invention.

More specifically liquefaction may be carried out as a three-step hot slurry process. The slurry is heated to between 60-95° C., preferably 80-85° C., and alpha-amylase is added to initiate liquefaction (thinning). Then the slurry may be jet-cooked at a temperature between 95-140° C., preferably 105-125° C., for 1-15 minutes, preferably for 3-10 minute, especially around 5 minutes. The slurry is cooled to 60-95° C. and more alpha-amylase is added to finalize hydrolysis (secondary liquefaction). The liquefaction process is usually carried out at pH 4.5-6.5, in particular at a pH between 5 and 6. Milled and liquefied whole grains are known as mash.

The saccharification in step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 30-65° C., typically around 60° C., and at a pH between 4 and 5, normally at about pH 4.5.

The most widely used process in fermentation product, especially ethanol, production is the simultaneous saccharification and fermentation (SSF) process, in which there is no holding stage for the saccharification, meaning that fermenting organism, such as yeast, and enzyme(s) may be added together. SSF may typically be carried out at a temperature between 25° C. and 40° C., such as between 29° C. and 35° C., such as between 30° C. and 34° C., such as around 32° C. According to the invention the temperature may be adjusted up or down during fermentation.

In accordance with the present invention the fermentation step (c) includes, without limitation, fermentation processes used to produce alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, beta-carotene); and hormones. Preferred fermentation processes include alcohol fermentation processes, as are well known in the art. Preferred fermentation processes are anaerobic fermentation processes, as are well known in the art.

Processes for Producing Fermentation Products from Un-Gelatinized Starch-Containing In this aspect the invention relates to processes for producing a fermentation product from starch-containing material without gelatinization of the starch-containing material (i.e., uncooked starch-containing material). In one embodiment only a glucoamylase of the invention is used during saccharification and fermentation. According to the invention the desired fermentation product, such as ethanol, can be produced without liquefying the aqueous slurry containing the starch-containing material. In one embodiment a process of the invention includes saccharifying (milled) starch-containing material, e.g., granular starch, below the gelatinization temperature in the presence of a glucoamylase of the invention to produce sugars that can be fermented into the desired fermentation product by a suitable fermenting organism.

Accordingly, in this aspect the invention relates to a process for producing a fermentation product from starch-containing material comprising:

(a) saccharifying starch-containing material with a mature glucoamylase according to the invention, preferably having the sequence shown as amino acids 20 to 634 of SEQ ID NO: 2, or amino acids 20 to 631 of SEQ ID NO: 4 or a glucoamylase having at least 90% identity thereto, at a temperature below the initial gelatinization temperature of said starch-containing material, (b) fermenting using a fermenting organism.

Steps (a) and (b) of the process of the invention may be carried out sequentially or simultaneously. In an embodiment a slurry comprising water and starch-containing material is prepared before step (a).

The fermentation process may be carried out for a period of 1 to 250 hours, preferably is from 25 to 190 hours, more preferably from 30 to 180 hours, more preferably from 40 to 170 hours, even more preferably from 50 to 160 hours, yet more preferably from 60 to 150 hours, even yet more preferably from 70 to 140 hours, and most preferably from 80 to 130 hours.

The term "initial gelatinization temperature" means the lowest temperature at which gelatinization of the starch commences. Starch heated in water begins to gelatinize between 50° C. and 75° C.; the exact temperature of gelatinization depends on the specific starch, and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material is the temperature at which birefringence is lost in 5% of the starch granules using the method described by Gorinstein and Lii, 1992, Starch/Stärke 44(12): 461-466 (1992).

Before step (a) a slurry of starch-containing material, such as granular starch, having 10-55 wt. % dry solids, preferably 25-40 wt. % dry solids, more preferably 30-35 wt. % dry solids of starch-containing material may be prepared. The slurry may include water and/or process waters, such as stillage (backset), scrubber water, evaporator condensate or distillate, side stripper water from distillation, or other fermentation product plant process water. Because the process of the invention is carried out below the gelatinization temperature and thus no significant viscosity increase takes place, high levels of stillage may be used if desired. In an embodiment the aqueous slurry contains from about 1 to about 70 vol. % stillage, preferably 15-60% vol. % stillage, especially from about 30 to 50 vol. % stillage.

The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids of the starch-containing material is converted into a soluble starch hydrolysate.

The process of the invention is conducted at a temperature below the initial gelatinization temperature. Preferably the temperature at which step (a) is carried out is between 30-75° C., preferably between 45-60° C.

In a preferred embodiment step (a) and step (b) are carried out as a sequential or simultaneous saccharification and fermentation process. In such preferred embodiment the process is typically carried at a temperature between 25° C. and 40° C., such as between 29° C. and 35° C., such as between 30° C. and 34° C., such as around 32° C. According to the invention the temperature may be adjusted up or down during fermentation.

In an embodiment simultaneous saccharification and fermentation is carried out so that the sugar level, such as glucose level, is kept at a low level such as below 6 wt. %, preferably below about 3 wt. %, preferably below about 2 wt. %, more preferred below about 1 wt. %, even more preferred below about 0.5 wt. %, or even more preferred 0.25% wt. %, such as below about 0.1 wt. %. Such low levels of sugar can be accomplished by simply employing adjusted quantities of enzyme and fermenting organism. A skilled person in the art can easily determine which quantities of enzyme and fermenting organism to use. The employed quantities of enzyme and fermenting organism may also be selected to maintain low concentrations of maltose in the fermentation broth. For instance, the maltose level may be kept below about 0.5 wt. % or below about 0.2 wt. %.

The process of the invention may be carried out at a pH in the range between 3 and 7, preferably from pH 3.5 to 6, or more preferably from pH 4 to 5.

Starch-Containing Materials

Any suitable starch-containing starting material, including granular starch, may be used according to the present invention. The starting material is generally selected based on the desired fermentation product. Examples of starch-containing starting materials, suitable for use in a process of present invention, include tubers, roots, stems, whole grains, corns, cobs, wheat, barley, rye, milo, sago, cassava, tapioca, sorghum, rice, peas, beans, or sweet potatoes, or mixtures thereof, or cereals, sugar-containing raw materials, such as molasses, fruit materials, sugar cane or sugar beet, potatoes, and cellulose-containing materials, such as wood or plant residues, or mixtures thereof. Contemplated are both waxy and non-waxy types of corn and barley.

The term "granular starch" means raw uncooked starch, i.e., starch in its natural form found in cereal, tubers or grains. Starch is formed within plant cells as tiny granules insoluble in water. When put in cold water, the starch granules may absorb a small amount of the liquid and swell. At temperatures up to 50° C. to 75° C. the swelling may be reversible. However, with higher temperatures an irreversible swelling called "gelatinization" begins. Granular starch to be processed may be a highly refined starch quality, preferably at least 90%, at least 95%, at least 97% or at least 99.5% pure or it may be a more crude starch containing material comprising milled whole grain including non-starch fractions such as germ residues and fibers. The raw material, such as whole grain, is milled in order to open up the structure and allowing for further processing. Two milling processes are preferred according to the invention: wet and dry milling. In dry milling whole kernels are milled and used. Wet milling gives a good separation of germ and meal (starch granules and protein) and is often applied at locations where the starch hydrolysate is used in production of syrups. Both dry and wet milling is well known in the art of starch processing and is equally contemplated for the process of the invention.

The starch-containing material is reduced in particle size, preferably by dry or wet milling, in order to expose more surface area. In an embodiment the particle size is between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen.

Fermentation Products

The term "fermentation product" means a product produced by a process including a fermentation step using a fermenting organism. Fermentation products contemplated according to the invention include alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes, as are well known in the art. Preferred fermentation processes are anaerobic fermentation processes, as are well known in the art.

Fermenting Organisms

"Fermenting organism" refers to any organism, including bacterial and fungal organisms, suitable for use in a fermentation process and capable of producing desired a fermentation product. Especially suitable fermenting organisms are able to ferment, i.e., convert, sugars, such as glucose or maltose, directly or indirectly into the desired fermentation product. Examples of fermenting organisms include fungal organisms, such as yeast. Preferred yeast includes strains of Saccharomyces spp., in particular, Saccharomyces cerevisiae. Commercially available yeast include, e.g., Red Star™/Lesaffre Ethanol Red (available from Red Star/Lesaffre, USA) FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties).

Enzymes

Glucoamylase

The glucoamylase is preferably a glucoamylase of the invention. However, as mentioned above a glucoamylase of the invention may also be combined with other glucoamylases. The term "glucoamylase" (1,4-alpha-D-glucan glucohydrolase, EC 3.2.1.3) is an enzyme, which catalyzes the release of D-glucose from the non-reducing ends of starch or related oligo- and polysaccharide molecules.

The glucoamylase may added in an amount of 0.001 to 10 AGU/g DS, preferably from 0.01 to 5 AGU/g DS, such as around 0.1, 0.3, 0.5, 1 or 2 AGU/g DS, especially 0.1 to 0.5 AGU/g DS or 0.02-20 AGU/g DS, preferably 0.1-10 AGU/g DS.

Alpha-Amylase

The alpha-amylase may be of any origin. Preferred are alpha-amylases of fungal or bacterial origin.

In a preferred embodiment the alpha-amylase is an acid alpha-amylase, e.g., fungal acid alpha-amylase or bacterial acid alpha-amylase. The term "acid alpha-amylase" means an alpha-amylase (EC 3.2.1.1) which added in an effective amount has activity optimum at a pH in the range of 3 to 7, preferably from 3.5 to 6, or more preferably from 4-5.

Bacterial Alpha-Amylases

A bacterial alpha-amylase may preferably be derived from the genus Bacillus.

In a preferred embodiment the Bacillus alpha-amylase is derived from a strain of B. licheniformis, B. amyloliquefaciens, B. subtilis or B. stearothermophilus, but may also be derived from other Bacillus sp. Specific examples of contemplated alpha-amylases include the Bacillus licheniformis alpha-amylase (BLA) shown in SEQ ID NO: 4 in WO 99/19467, the Bacillus amyloliquefaciens alpha-amylase (BAN) shown in SEQ ID NO: 5 in WO 99/19467, and the Bacillus stearothermophilus alpha-amylase (BSG) shown in SEQ ID NO: 3 in WO 99/19467. In an embodiment of the invention the alpha-amylase is an enzyme having a degree of identity of at least 60%, preferably at least 70%, more preferred at least 80%, even more preferred at least 90%, such as at least 95%, at least 96%, at least 97%, at least 98% or at least 99% identity to any of the sequences shown as SEQ ID NO: 1, 2, 3, 4, or 5, respectively, in WO 99/19467.

The Bacillus alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,187,576, and 6,297,038 (hereby incorporated by reference) and include Bacillus stearothermophilus alpha-amylase (BSG alpha-amylase) variants having a deletion of one or two amino acid in position 179 to 182, preferably a double deletion disclosed in WO 96/23873—see, e.g., page 20, lines 1-10 (hereby incorporated by reference), preferably corresponding to delta (181-182) compared to the wild-type BSG alpha-amylase amino acid sequence set forth in SEQ ID NO: 3 disclosed in WO 99/19467 or deletion of amino acids 179 and 180 using SEQ ID NO: 3 in WO 99/19467 for numbering (which reference is hereby incorporated by reference). Even more preferred are Bacillus alpha-amylases, especially Bacillus stearothermophilus alpha-amylase, which have a double deletion corresponding to delta (181-182) and further comprise a N193F substitution (also denoted I181*+G182*+N193F) compared to the wild-type BSG alpha-amylase amino acid sequence set forth in SEQ ID NO: 3 disclosed in WO 99/19467.

The alpha-amylase may also be a maltogenic alpha-amylase. A "maltogenic alpha-amylase" (glucan 1,4-alpha-maltohydrolase, EC 3.2.1.133) is able to hydrolyze amylose and amylopectin to maltose in the alpha-configuration. A maltogenic alpha-amylase from Bacillus stearothermophilus strain NCIB 11837 is commercially available from Novozymes A/S, Denmark. The maltogenic alpha-amylase is described in U.S. Pat. Nos. 4,598,048, 4,604,355 and 6,162,628, which are hereby incorporated by reference.

Bacterial Hybrid Alpha-Amylases

A hybrid alpha-amylase specifically contemplated comprises 445 C-terminal amino acid residues of the Bacillus licheniformis alpha-amylase (shown as SEQ ID NO: 4 in WO 99/19467) and the 37 N-terminal amino acid residues of the alpha-amylase derived from Bacillus amyloliquefaciens (shown as SEQ ID NO: 3 in WO 99/19467), with one or more, especially all, of the following substitutions: G48A+T49I+G107A+H156Y+A181T+N190F+I201F+A209V+Q264S (using the Bacillus licheniformis numbering). Also preferred are variants having one or more of the following mutations (or corresponding mutations in other Bacillus alpha-amylase backbones): H154Y, A181T, N190F, A209V and Q264S and/or deletion of two residues between positions 176 and 179, preferably deletion of E178 and G179 (using the SEQ ID NO: 5 numbering of WO 99/19467).

The bacterial alpha-amylase may be added in amounts as are well-known in the art.

Fungal Alpha-Amylases

Fungal acid alpha-amylases include acid alpha-amylases derived from a strain of the genus *Aspergillus*, such as *Aspergillus kawachii*, *Aspergillus niger*, or *Aspergillus oryzae* alpha-amylases.

A preferred acid fungal alpha-amylase is a Fungamyl-like alpha-amylase which is preferably derived from a strain of *Aspergillus oryzae*. In the present disclosure, the term "Fungamyl-like alpha-amylase" indicates an alpha-amylase which exhibits a high identity, i.e., more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874.

Another preferred acid alpha-amylase is derived from a strain *Aspergillus niger*. In a preferred embodiment the acid fungal alpha-amylase is the one from *A. niger* disclosed as "AMYA_ASPNG" in the Swiss-prot/TeEMBL database under the primary accession no. P56271 and described in more detail in WO 89/01969 (Example 3). The acid *Aspergillus niger* acid alpha-amylase is also shown as SEQ ID NO: 1 in WO 2004/080923 (Novozymes) which is hereby incorporated by reference. Also variants of said acid fungal amylase having at least 70% identity, such as at least 80% or even at least 90% identity, such as at least 95%, at least 96%, at least 97%, at least 98%, or at least 99% identity to SEQ ID NO: 1 in WO 2004/080923 are contemplated. A suitable commercially available acid fungal alpha-amylase derived from *Aspergillus niger* is SP288 (available from Novozymes A/S, Denmark).

In a preferred embodiment the alpha-amylase is derived from *Aspergillus kawachii* and disclosed by Kaneko et al., 1996, *J. Ferment. Bioeng.* 81: 292-298, "Molecular-cloning and determination of the nucleotide-sequence of a gene encoding an acid-stable alpha-amylase from *Aspergillus kawachii*"; and further as EMBL:#AB008370.

The fungal acid alpha-amylase may also be a wild-type enzyme comprising a carbohydrate-binding module (CBM) and an alpha-amylase catalytic domain (i.e., a none-hybrid), or a variant thereof. In an embodiment the wild-type acid alpha-amylase is derived from a strain of *Aspergillus kawachii*.

Fungal Hybrid Alpha-Amylases

In a preferred embodiment the fungal acid alpha-amylase is a hybrid alpha-amylase. Preferred examples of fungal hybrid alpha-amylases include the ones disclosed in WO 2005/003311 or U.S. Application Publication no. 2005/0054071 (Novozymes) or U.S. application No. 60/638,614 (Novozymes) which is hereby incorporated by reference. A hybrid alpha-amylase may comprise an alpha-amylase catalytic domain (CD) and a carbohydrate-binding domain/module (CBM) and optional a linker.

Specific examples of contemplated hybrid alpha-amylases include those disclosed in U.S. application No. 60/638,614 including Fungamyl variant with catalytic domain JA118 and *Athelia rolfsii* SBD (SEQ ID NO: 100 in U.S. application No. 60/638,614), *Rhizomucor pusillus* alpha-amylase with *Athelia rolfsii* AMG linker and SBD (SEQ ID NO: 101 in U.S. application No. 60/638,614) and *Meripilus giganteus* alpha-amylase with *Athelia rolfsii* glucoamylase linker and SBD (SEQ ID NO: 102 in U.S. application No. 60/638,614).

Other specific examples of contemplated hybrid alpha-amylases include those disclosed in U.S. Application Publication no. 2005/0054071, including those disclosed in Table 3 on page 15, such as *Aspergillus niger* alpha-amylase with *Aspergillus kawachii* linker and starch binding domain.

Commercial Alpha-Amylase Products

Preferred commercial compositions comprising alpha-amylase include MYCOLASE from DSM (Gist Brocades), BAN™, TERMAMYL™ SC, FUNGAMYL™, LIQUOZYME™ X and SAN™ SUPER, SAN™ EXTRA L (Novozymes A/S) and CLARASE™ L-40,000, DEX-LO™, SPEZYME™ FRED, SPEZYME™ AA, SPEZYME™ Ethyl, GC358, GC980, SPEZYME™ RSL, and SPEZYME™ DELTA AA (Genencor Int.), and the acid fungal alpha-amylase sold under the trade name SP288 (available from Novozymes A/S, Denmark).

An acid alpha-amylase may according to the invention be added in an amount of 0.1 to 10 AFAU/g DS, preferably 0.10 to 5 AFAU/g DS, especially 0.3 to 2 AFAU/g DS.

Production of Syrup

The present invention also provides a process of using a glucoamylase of the invention for producing syrup, such as glucose and the like, from starch-containing material. Suitable starting materials are exemplified in the "Starch-containing materials"-section above. Generally, the process comprises the steps of partially hydrolyzing starch-containing material (liquefaction) in the presence of alpha-amylase and then further saccharifying the release of glucose from the non-reducing ends of the starch or related oligo- and polysaccharide molecules in the presence of glucoamylase of the invention.

Liquefaction and saccharification may be carried our as described above for fermentation product production.

The glucoamylase of the invention may also be used in immobilized form. This is suitable and often used for producing speciality syrups, such as maltose syrups, and further for the raffinate stream of oligosaccharides in connection with the production of fructose syrups, e.g., high fructose syrup (HFS).

Consequently, this aspect of the invention relates to a process of producing syrup from starch-containing material, comprising (a) liquefying starch-containing material in the presence of an alpha-amylase, and (b) saccharifying the material obtained in step (a) using a glucoamylase of the invention.

A syrup may be recovered from the saccharified material obtained in step (b).

Details on suitable conditions can be found above.

Brewing

A glucoamylase of the invention can also be used in a brewing process. The glucoamylase of the invention is added in effective amounts which can be easily determined by the skilled person in the art.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties. The present invention is further described by the following examples which should not be construed as limiting the scope of the invention.

Signal Peptide and Propeptide

The present invention also relates to an isolated polynucleotide encoding a signal peptide comprising or consisting of amino acids 1 to 19 of SEQ ID NO: 2 or 1 to 19 of SEQ ID NO: 4. The polynucleotides may further comprise a gene encoding a protein, which is operably linked to the signal peptide. The protein is preferably foreign to the signal peptide and/or propeptide. In one aspect, the polynucleotide encoding the signal peptide is nucleotides 1 to 57 of SEQ ID NO: 1 or 1 to 57 of SEQ ID NO: 3.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenol oxidase, proteolytic enzyme, ribonuclease, transglutaminase, xylanase, or beta-xylosidase.

The gene may be obtained from any prokaryotic, eukaryotic, or other source.

The present invention is further described by the following examples.

EXAMPLES

Glucoamylase Activity

Glucoamylase activity may be measured in AGI units or in Glucoamylase Units (AGU), or according to other suitable assays like e.g. a commercial assay kit from Kikkoman.

Glucoamylase Activity (AGI)

Glucoamylase (equivalent to amyloglucosidase) converts starch into glucose. The amount of glucose is determined here by the glucose oxidase method for the activity determination. The method described in the section 76-11 Starch—Glucoamylase Method with Subsequent Measurement of Glucose with Glucose Oxidase in "Approved methods of the American Association of Cereal Chemists". Vol. 1-2 AACC, from American Association of Cereal Chemists, (2000); ISBN: 1-891127-12-8.

One glucoamylase unit (AGI) is the quantity of enzyme which will form 1 micro mole of glucose per minute under the standard conditions of the method.

Standard Conditions/Reaction Conditions:
Substrate: Soluble starch, concentration approx. 16 g dry matter/L.
Buffer: Acetate, approx. 0.04M, pH=4.3
pH: 4.3
Incubation temperature: 60° C.
Reaction time: 15 minutes
Termination of the reaction: NaOH to a concentration of approximately 0.2 g/L (pH-9)
Enzyme concentration: 0.15-0.55 AAU/mL.

The starch should be Lintner starch, which is a thin-boiling starch used in the laboratory as colorimetric indicator. Lintner starch is obtained by dilute hydrochloric acid treatment of native starch so that it retains the ability to color blue with iodine.

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

Glucoamylase Activity Assay (Kikkoman)
Product code: 60211
This kit is for measurement of the glucose-forming activity in rice koji.
Assay Principle:

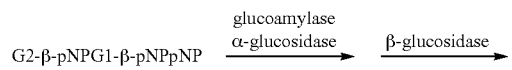

The substrate, 4-nitrophenyl-β-maltoside (G2-β-pNP) is degraded by glucoamylase or α-glucosidase into 4-nitrophenyl-β-glucoside (G1-(3-pNP). G1-6-pNP is further degraded into 4-nitrophenol (pNP) by β-glucosidase in this kit. Reaction is performed at room temperature at pH about 4. The reaction is stopped by addition of sodium carbonate, and at the same time the solution becomes alkaline pH to maximize the absorbance of pNP. The glucose-forming activity is measured by quantifying the pNP at 400 nm.

1) The measured response shows the G2-β-pNP degradation activity of glucoamylase and α-glucosidase in the sample. This is thought to be the glucose forming activity in the sample.

2) The test can be used for rice koji extract without dialysis.

3) This assay is not affected by α-amylase in the sample.

Kit Components

| Reagent | Main component | Amount |
| --- | --- | --- |
| substrate solution | G2-β-pNP | 60 ml |
| enzyme solution | β-glucosidase | 60 ml |
| stop solution | sodium carbonate | 120 ml |

1) Mix "substrate solution" and "enzyme solution" of the kit at 1:1.
2) Pipette 20 μl of the sample (or water as a blank) and transfer it to a microtiter plate well. (duplicate)
3) Add 60 μl of the substrate-enzyme mixture to the well.
4) Incubate at room temperature for 20 min.
5) Add 120 μl of the stop solution to the well.
6) Read OD400 nm. # Net $OD_{400}=OD_{400}$(sample)–$OD_{400}$ (blank)
1. Blank: Usually, the blank absorbance is less than 0.200.
2. Specificity: The response is not affected by glucose (up to 100 g/l) or α-amylase (725 U/ml).
3. Reproducibility: The CV of absorbance is less than 1% when the same sample is analyzed 10 times.
4. Linear range: The net $OD_{400}$ up to 1.6 should be proportional to the enzyme concentration.
5. Stability of color: The absorbance does not change for 2 h at 25° C.

Wako Glucose Assay Kit (LabAssay Glucose, WAKO, Cat#298-65701).

LabAssay™ Glucose is a reagent kit for assay of glucose based on an enzymatic method with a combination of mutarotase and glucose oxidase.

α-D-glucose and β-D-glucose in solution maintain equilibrium in a constant ratio. Glucose oxidase reacts only with β-D-glucose and does not react with α-D-glucose. Therefore, α-D-glucose is converted into β-D-glucose using mutarotase.

When a sample is mixed with the Chromogen Reagent, the alpha-form of glucose in the sample is converted to beta-form by mutarotase. Beta-D-glucose is oxidized and yields hydrogen peroxide by glucose oxidase (GOD). In the presence of peroxidase (POD), the formed hydrogen peroxide yields a red pigment by quantitative oxidation condensation with phenol and 4-aminoantipyrine. The glucose concentration is obtained by measuring absorbance of the red pigment.

The assay was performed in 96 wells microplates using a microplate reader with 505 nm wavelength filter. Assay was performed at 37° C. for 5 min.

The principle of the assay method is further described in Miwa, et al., 1972, Clin. Chim. Acta., 37, 538-540.

Materials

Chemicals used as buffers and substrates were commercial products of at least reagent grade.

Strains

*Chaetomium thermophilum* (CBS144.50) was used as the source of polypeptides having glucoamylase activity. *Aspergillus niger* strain HowB112 was used for expression of the *Chaetomium thermophilum* genes encoding the polypeptides having glucoamylase activity. *A. niger* HowB112 is an amdS (acetamidase) gene disrupted derivative of *A. niger* BO1. Strain HowB112 bears following genotypes: AMG⁻ (disrupted glucoamylase gene), ASA⁻ (disrupted acid stable amylase gene) and tgs⁻ (disrupted alpha-1,6-transglucosidase gene).

Media and Solutions

YMD medium was composed of 0.3% yeast extract, 0.5% peptone, of 0.3% malt extract and 5% maltodextrin.

PDA agar plates were composed of potato infusion (potato infusion was made by boiling 300 g of sliced (washed but unpeeled) potatoes in water for 30 minutes and then decanting or straining the broth through cheesecloth. Distilled water was then added until the total volume of the suspension was one liter, followed by 20 g of dextrose and 20 g of agar powder. The medium was sterilized by autoclaving at 15 psi for 15 minutes (Bacteriological Analytical Manual, 8th Edition, Revision A, 1998).

LB plates were composed of 10 g of Bacto-Tryptone, 5 g of yeast extract, 10 g of sodium chloride, 15 g of Bacto-agar, and deionized water to 1 liter.

LB medium was composed of 10 g of Bacto-Tryptone, 5 g of yeast extract, and 10 g of sodium chloride, and deionized water to 1 liter.

YPG medium contained 0.4% of yeast extract, 0.1% of KH2PO4, 0.05% of $MgSO_4.7H_2O$, 1.5% glucose in deionized water COVE-N-gly slants were composed of 218 g sorbitol, 10 g glycerol, 2.02 g KNO3, 50 ml COVE salt solution, 25 g agar powder and deionized water to 1 liter.

COVE plates for protoplast regeneration were composed of 342 g of sucrose, 20 g of agar powder, 20 ml of COVE salt solution, and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide, 15 mM CsCl, were added.

COVE top agarose were composed of 342.3 g sucrose, 20 ml COVE salt solution, 6 g GTG agarose (SeaKem, Cat#50070) and deionized water to 1 liter. The medium was sterilized by autoclaving at 15 psi for 15 minutes (Bacteriological Analytical Manual, 8th Edition, Revision A, 1998). The medium was cooled to 60° C., and 10 mM acetamide and 15 mM CsCl were added.

COVE-2 plate for isolation were composed of 30 g sucrose, 20 ml COVE salt solution, 30 g agar powder and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide was added.

COVE salt solution was composed of 26 g of $MgSO_4.7H_2O$, 26 g of KCL, 26 g of $KH_2PO_4$, 50 ml of COVE trace metal solution, and deionized water to 1 liter.

COVE trace metal solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_4.2H_2O$, 10 g of $ZnSO_4.7H_2O$, and deionized water to 1 liter.

Example 1

*Chaetomium thermophilum* Genomic DNA Extraction

*Chaetomium thermophilum* strain CBS144.50 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH® (Calbiochem, La Jolla, Calif., USA) and frozen in liquid nitrogen. Frozen mycelia were ground, by a mortar and a pestle, to a fine powder, and genomic DNA was isolated using DNeasy® Plant Maxi Kit (QIAGEN Inc., Valencia, Calif., USA) following the manufacturer's instruction.

Example 2

Genome Sequencing, Assembly and Annotation

The extracted genomic DNA samples were delivered to Beijing Genome Institute (BGI, Shenzhen, China) for genome sequencing using ILLUMINA® GA2 System (Illumina, Inc., San Diego, Calif., USA). The raw reads were assembled at BGI using in house program SOAPdenovo. The assembled sequences were analyzed using standard bioinformatics methods for gene finding and functional prediction. Briefly, gene ID (Parra et al., 2000, Genome Research 10(4):511-515) was used for gene prediction. Blastall version 2.2.10 (National Center for Biotechnology Information (NCBI) Bethesda, Md., USA) and HMMER version 2.1.1 (National Center for Biotechnology Information (NCBI) Bethesda, Md., USA) were used to predict function based on structural homology. The family GH15 glucoamylase candidates were identified directly by analysis of the Blast results. A gene (Munch and Krogh, 2006, BMC Bioinformatics 7:263) and SignalP (Nielsen et al., 1997, Protein Engineering 10:1-6) were used to identify starting codons. SignalP was further used to estimate length of signal peptide. Pepstats (European Bioinformatics Institute, Hinxton, Cambridge CB10 1SD, UK) was used to estimate isoelectric point of proteins, and molecular weight.

2 annotated GH15 glucoamylase genes (shown in Table 1) were selected for expression cloning.

TABLE 1

GH15 glucoamylase genes from Chaetomium thermophilum

| Gene name | DNA sequence |
|---|---|
| AMG56053-1 | SEQ ID: 1 |
| AMG56053-2 | SEQ ID: 3 |

Example 3

Cloning of 2 GH15 Glucoamylase Genes from the Chaetomium thermophilum Genomic DNA Based on the DNA information obtained from genome sequencing, oligonucleotide primers, shown below in table 2, were designed to amplify the 2 GH15 glucoamylase genes (SEQ ID: 1 and 3) from the genomic DNA of Chaetomium thermophilum CBS144.50. Primers were synthesized by Invitrogen (Invitrogen, Beijing, China).

TABLE 2

Primers to amplify full-length glucoamylase genes from Chaetomium thermophilum genomic DNA

| Related SEQ ID | Primer name | Sequence (5'-3') |
|---|---|---|
| SEQ ID NO: 5 | AMG56053-1_C505_bam | acacaactggggaTCACCATGCCTCTCTCGTCACTC |
| SEQ ID NO: 6 | AMG56053-1_C505_xho | ccctctagatctcgaGAAATCTAACGCCACGAAGCCTCCT |
| SEQ ID NO: 7 | AMG56053-2_P355_BamH | acacaactggggatccaccATGCCATTGATTAAAACACTGGCATTAAC |
| SEQ ID NO: 8 | AMG56053-2_P355_BgIII | gtcaccctctagatctcgagACTCGGCCAATCTCGGCTTTA |

Upper characters represent the 5'- and 3'-regions of the to be amplified genes, while lower cases were homologous to the vector sequences at insertion sites of pCaHj505 vector. The expression vector pCaHj505 containins the TAKA-amylase promoter derived from Aspergillus oryzae and the Aspergillus niger glucoamylase terminator elements. Furthermore pCaHj505 has pUC18 derived sequences for selection and propagation in E. coli, and an amdS gene, which encodes an acetoamidase gene derived from Aspergillus nidulans for selection of an amdS+ Aspergillus transformant.

For each gene, 20 pmol of primer pair (each of the forward and reverse) were used in a PCR reaction composed of 2 μl of Chaetomium thermophilum CBS144.50 genomic DNA, 10 μl of 5×GC Buffer, 1.5 μl of DMSO, 2.5 mM each of dATP, dTTP, dGTP, and dCTP, and 0.6 unit of Phusion™ High-Fidelity DNA Polymerase (FinnzymesOy, Espoo, Finland) in a final volume of 50 μl. The amplification was performed using a Peltier Thermal Cycler (M J Research Inc., South San Francisco, Calif., USA) programmed for denaturing at 98° C. for 1 minutes; 10 cycles of denaturing at 98° C. for 15 seconds, annealing at 65° C. for 30 seconds, with 1° C. decrease per cycle and elongation at 72° C. for 90 seconds; and another 26 cycles each at 98° C. for 15 seconds, 60° C. for 30 seconds and 72° C. for 90 seconds; final extension at 72° C. for 10 minutes. The heat block then went to a 4° C. soak cycle.

The PCR products were isolated by 0.7% agarose gel electrophoresis using 90 mM Tris-borate and 1 mM EDTA (TBE) buffer where product bands at expected size of each PCR reaction were visualized under UV light. The PCR products were then purified from solution by using a GFX PCR DNA and Gel Band Purification Kit (GE Healthcare, Buckinghamshire, UK) according to the manufacturer's instructions.

TABLE 3

Size of PCR products in Example 3

| Gene name | Size of PCR product |
|---|---|
| AMG56053-1 | 2 kb |
| AMG56053-2 | 2 kb |

Plasmid pCaHj505 was digested with BamHI and XhoI, isolated by 0.7% agarose gel electrophoresis using TBE buffer, and purified using an Illustra™ PCR DNA and Gel Band Purification Kit according to the manufacturer's instructions.

An In-Fusion™ CF Dry-down Cloning Kit (Clontech Laboratories, Inc., Mountain View, Calif., USA) was used to clone the fragment directly into the expression vector pCaHj505.

The PCR products and the digested vector were ligated together using an IN-FUSION™ CF Dry-down Cloning Kit (Clontech Laboratories, Inc., Mountain View, Calif., USA) resulting in plasmids in Table 4 respectively, in which transcription of *Humicola insolens* GH15 glucoamylase genes was under the control of a TAKA-amylase promoter from *Aspergillus otyzae*. The cloning operation was according to the manufacturer's instruction. In brief, for each ligation reaction 30 ng of with BamHI and XhoI digested pCaHj505 and 60 ng of purified PCR products were added to the reaction vial and resuspended with the powder in a final volume of 10 μl with addition of deionized water. The reactions were incubated at 37° C. for 15 minutes and then 50° C. for 15 minutes. 3 μl of the reaction were transformed into *E. coli* TOP10 competent cells (TIANGEN Biotech (Beijing) Co. Ltd., Beijing, China) according to the manufacturer's protocol and plated onto LB plates supplemented with 0.1 mg of ampicillin per ml. After incubating at 37° C. overnight, colonies were seen growing on the LB ampicillin plates. *E. coli* transformants containing expression constructs were detected by colony PCR and confirmed by DNA sequencing with vector primers (by SinoGenoMax Company Limited, Beijing, China). Plasmid DNA pAMG56053-1_C505 and pAMG56053-2_C505 for expression in *A. niger* were extracted from correct *E. coli* transformants, by using a QIAprep Spin Miniprep Kit (QIAGEN Inc., Valencia, Calif., USA).

TABLE 4

| Plasmid (Expression constructs) in Example 3 | |
|---|---|
| Gene name | Plasmid |
| AMG56053-1 | pAMG56053-1_C505 |
| AMG56053-2 | pAMG56053-2_C505 |

Example 4

Expression of *Chaetomium thermophilum* GH15 Glucoamylse Genes in *Aspergillus niger*

An agar slant (COVE-N-gly) was inoculated with spores of *Aspergillus niger* HowB112, and grown at 32° C. until it was completely sporulated. The spores were resuspended in 5-10 ml of sterile 0.05% tween20 water. About $10^8$ spores were transferred to a 500 ml baffled shake flask containing 100 ml YPG medium with 10 mM $NaNO_3$, and incubated at 32° C. for 16 hrs at 99 rpm in Innova shaker. Then the mycelia were harvested for protoplasts preparation. *Aspergillus niger* HowB112 protoplasts preparation and transformation were done according to the method described in patent WO2004/111218 or EP 238023. 10 μg of pAMG56053-1_C505 was used to transform *Aspergillus niger* HowB112 separately.

The *Aspergillus niger* HowB112 transformants with pAMG56053-1_C505 were selected on the COVE plates for protoplast regeneration (described in the Media and Solution part). About 10 transformants were observed on the selective plates for each transformation. Six transformants from each transformation were isolated on COVE-2 plate for 3-4 days at 32° C.

After isolation those six transformants for each transformation were inoculated separately into 3 ml of YMD medium in 24-well plate and incubated at 30° C., 220 rpm. After 3 days incubation, 20 μl of supernatant from each culture were analyzed on NuPAGENovex 4-12% Bis-Tris Gel w/MES (Invitrogen Corporation, Carlsbad, Calif., USA) according to the manufacturer's instructions. The resulting gel was stained with Instant Blue (Expedeon Ltd., Babraham Cambridge, UK). SDS-PAGE profiles of the cultures showed that they had the excepted protein bands of expression products ofpAMG56053-1_C505. The expression product number and expression strain number was shown in Table 5.

TABLE 5

| Expression strains | | |
|---|---|---|
| Expression construct | Expression product | Expression strain |
| pAMG56053-1_C505 | P23S9D (SEQ ID NO: 2) | O4J6F |

Example 5

Fermentation of *A. niger* Expression Strains

A slant of O4J6F was washed with 10 ml of YMD and inoculated into a 2 liter flask containing 400 ml of YMD medium to generate broth for characterization of the enzyme. The culture was incubated at 30° C. on shaker at 150 rpm. The culture was harvested on day 3 and filtered using a 0.45 μm DURAPORE Membrane (Millipore, Bedford, Mass., USA). The filtered culture broth was used for enzyme characterization.

Example 6

Characterization of Glucoamylases

Substrate: 1% soluble starch (Sigma S-9765) in deionized water
Reaction buffer: 0.1M Acetate buffer at pH4.3
Glucose concentration determination kit: Wako glucose assay kit (LabAssay glucose, WAKO, Cat#298-65701).
Reaction Condition:
20 μl soluble starch and 50 μl acetate buffer at pH5.3 were mixed. 30 μl enzyme solution (50 μg enzyme protein/mil) was added to a final volume of 100 μl followed by incubation at 37° C. for 15 min.
The glucose concentration is determined by Wako kits.
All the experiments were carried out in parallel.
Temperature Optimum.
To assess the temperature profile, the Reaction condition assay described above was performed at 20, 30, 40, 50, 60, 70, 80, and 90° C. The results are shown in table 6.

TABLE 6

| Temperature optimum | | | | | | | | | |
|---|---|---|---|---|---|---|---|---|---|
| Temperature (° C.) | | 20 | 30 | 40 | 50 | 60 | 70 | 80 | 90 |
| Relative activity (%) | P23S9D | 46.2 | 52.0 | 63.6 | 82.0 | 91.5 | 100 | 91.7 | 73.0 |

From the result it can be seen that the optimal temperature for P23S9Dat the given conditions is around 70° C.

Heat Stability:

To assess the heat stability of these glucoamylases the Reaction condition assay was modified in that the enzyme solution and acetate buffer was preincubated at 70° C. for 0, 10, 30, 60, and 120 minutes. Following the incubation 20 μl of starch was added to the solution and the assay was performed as described above.

The results were shown in table 7.

TABLE 7

| Heat stability | | | | | |
|---|---|---|---|---|---|
| Incubation time (min) | 0 | 10 | 30 | 60 | 120 |
| Relative activity (%) P23S9D (70° C.) | 100 | 42.1 | 41.2 | 43.6 | 42.5 | pH Optimum:

To assess the pH optimum of the glucoamylases the Reaction condition assay described above was performed at pH 2.0, 3.0, 4.0, 5.0, 6.0 7.0, 8.0, 9.0, 10.0 and 11.0. Instead of using the acetate buffer described in the Reaction condition assay the following buffer was used 100 mM Succinic acid, HEPES, CHES, CAPSO, 1 mM $CaCl_2$, 150 mM KCl, 0.01% Triton X-100, pH adjusted to 2.0, 3.0, 3.5, 4.0, 4.5, 5.0, 6.0 7.0, 8.0, 9.0, 10.0 or 11.0 with HCl or NaOH. The results were shown in table 8.

TABLE 8

| pH optimum | | | | | | | | | | |
|---|---|---|---|---|---|---|---|---|---|---|
| pH | 2.0 | 3.0 | 4.0 | 5.0 | 6.0 | 7.0 | 8.0 | 9.0 | 10.0 | 11.0 |
| Relative activity (%) P23S9D | 58.5 | 53.6 | 86.8 | 99.5 | 97.7 | 98.6 | 100 | 68.8 | 69.7 | 59.3 |

From the result it can be seen that P23S9D has a very broad pH profile.

pH Stability:

30 μl enzyme solution (50 μg/ml) and 50 μl buffer at was mixed and preincubated for 0, 10, 30, 60, 120 mins. After preincubation, 20 μl soluble starch in a final volume of 100 μl was incubated at 37° C. for 15 min.

Finally the glucose concentration was determined using the Wako kits. The results are shown in table 9.

TABLE 9

| pH stability | | | | | |
|---|---|---|---|---|---|
| Incubation time (min) | 0 | 10 | 30 | 60 | 120 |
| Relative activity (%) P23S9D (pH 5) | 100 | 99.4 | 99.2 | 98.6 | 98.6 |

From the result it can be seen that the glucoamylase is stable at acidic condition under the conditions tested.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The present invention is further described by the following numbered paragraphs.

[1] An isolated polypeptide having glucoamylase activity, selected from the group consisting of:
   (a) a polypeptide having at least 76% sequence identity to the mature polypeptide of SEQ ID NO: 2 or SEQ ID NO: 4;
   (b) a polypeptide encoded by a polynucleotide that hybridizes under medium stringency conditions, high stringency conditions, or very high stringency conditions with (i) the mature polypeptide coding sequence of SEQ ID NO: 1 or SEQ ID NO: 3, (ii) the cDNA sequence thereof, or (iii) the full-length complement of (i) or (ii);
   (c) a polypeptide encoded by a polynucleotide having at least 76% sequence identity to the mature polypeptide coding sequence of SEQ ID NO: 1 or SEQ ID NO: 3, or the cDNA sequence thereof;
   (d) a variant of the mature polypeptide of SEQ ID NO: 2 or SEQ ID NO: 4 comprising a substitution, deletion, and/or insertion at one or more positions; and
   (e) a fragment of the polypeptides of (a), (b), (c), or (d) that has glucoamylase activity.

[2] The polypeptide of paragraph 1, having at least 78%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2 or SEQ ID NO: 4.

[3] The polypeptide of paragraph 1 or 2, which is encoded by a polynucleotide that hybridizes under medium-high stringency conditions, high stringency conditions, or very high stringency conditions with (i) the mature polypeptide coding sequence of SEQ ID NO: 1 or SEQ ID NO: 3, (ii) the cDNA sequence thereof, or (iii) the full-length complement of (i) or (ii).

[4] The polypeptide of any of paragraphs 1-3, which is encoded by a polynucleotide having at least 78%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or SEQ ID NO: 3, or the cDNA sequence thereof.

[5] The polypeptide of any of paragraphs 1-4, comprising or consisting of SEQ ID NO: 2 or SEQ ID NO: 4, or the mature polypeptide of SEQ ID NO: 2 or SEQ ID NO: 4.

[6] The polypeptide of paragraph 5, wherein the mature polypeptide is amino acids 20 to 634 of SEQ ID NO: 2 or amino acids 20 to 631 of SEQ ID NO: 4.

[7] The polypeptide of any of paragraphs 1-4, which is a variant of the mature polypeptide of SEQ ID NO: 2 or SEQ ID NO: 4 comprising a substitution, deletion, and/or insertion at one or more (several) positions.

[8] The polypeptide of paragraph 1, which is a fragment of SEQ ID NO: 2 or SEQ ID NO: 4, wherein the fragment has glucoamylase activity activity.

[9] An isolated polypeptide comprising a catalytic domain selected from the group consisting of:
- (a) a catalytic domain having at least 76% sequence identity to amino acids 33 to 505 of SEQ ID NO: 2 or amino acids 28 to 504 of SEQ ID NO: 4;
- (b) a catalytic domain encoded by a polynucleotide that hybridizes under medium stringency conditions with (i) nucleotides 97 to 1609 of SEQ ID NO: 1 or nucleotides 82 to 1680 of SEQ ID NO: 3, (ii) the cDNA sequences thereof, or (iii) the full-length complement of (i) or (ii);
- (c) a catalytic domain encoded by a polynucleotide having at least 76% sequence identity to the catalytic domain of SEQ ID NO: 1 or of SEQ ID NO: 3 or the cDNA sequences thereof;
- (d) a variant of amino acids 33 to 505 of SEQ ID NO: 2 or amino acids 28 to 504 of SEQ ID NO: 4 comprising a substitution, deletion, and/or insertion at one or more (e.g., several) positions; and
- (e) a fragment of the catalytic domain of (a), (b), (c), or (d) that has glucoamylase activity.

[10] The polypeptide of paragraph 9, further comprising a carbohydrate binding domain.

[11] A composition comprising the polypeptide of any of paragraphs 1-10.

[12] A composition according to paragraph 11, comprising an alpha-amylase and a polypeptide of any of paragraphs 1-10.

[13] A use of a polypeptide of any of paragraphs 1-10 for production of syrup and/or a fermentation product.

[14] The use according to paragraph 13, wherein the starting material is gelatinized or un-gelatinized starch-containing material.

[15] A use of a polypeptide of any of paragraphs 1-10 for brewing.

[16] A process of producing a fermentation product from starch-containing material comprising the steps of:
- (a) liquefying starch-containing material;
- (b) saccharifying the liquefied material; and
- (c) fermenting with a fermenting organism;

wherein step (b) is carried out using at least a glucoamylase of any of paragraphs 1-10.

[17] A process of producing a fermentation product from starch-containing material, comprising the steps of:
- (a) saccharifying starch-containing material at a temperature below the initial gelatinization temperature of said starch-containing material; and
- (b) fermenting with a fermenting organism, wherein step (a) is carried out using at least a glucoamylase of any of paragraphs 1-10.

[18] An isolated polynucleotide encoding the polypeptide of any of paragraphs 1-10.

[19] A nucleic acid construct or expression vector comprising the polynucleotide of paragraph 18 operably linked to one or more control sequences that direct the production of the polypeptide in an expression host.

[20] A recombinant host cell comprising the polynucleotide of paragraph 18 operably linked to one or more control sequences that direct the production of the polypeptide.

[21] A method of producing the polypeptide of any of paragraphs 1-10, comprising:
- (a) cultivating a cell, which in its wild-type form produces the polypeptide, under conditions conducive for production of the polypeptide; and
- (b) recovering the polypeptide.

[22] A method of producing a polypeptide of any of paragraphs 1-10, comprising:
- (a) cultivating the host cell of paragraph 20 under conditions conducive for production of the polypeptide; and
- (b) recovering the polypeptide.

[23] A transgenic plant, plant part or plant cell comprising a polynucleotide encoding the polypeptide of any of paragraphs 1-10.

[24] A method of producing a polypeptide of any of paragraphs 1-10, comprising:
- (a) cultivating the transgenic plant or plant cell of paragraph 23 under conditions conducive for production of the polypeptide; and
- (b) recovering the polypeptide.

The invention claimed is:

1. A process of producing a fermentation product from starch-containing material comprising the steps of:
   (a) liquefying starch-containing material;
   (b) saccharifying the liquefied material; and
   (c) fermenting with a fermenting organism;
wherein step (b) is carried out by contacting the liquefied material with at least a glucoamylase having at least 85% sequence identity to the mature polypeptide of SEQ ID NO: 2 or SEQ ID NO: 4, and wherein the fermentation product is ethanol.

2. The process of claim 1 wherein the glucoamylase has at least 90% sequence identity to the mature polypeptide of SEQ ID NO: 2.

3. The process of claim 1 wherein the glucoamylase has at least 95% sequence identity to the mature polypeptide of SEQ ID NO: 2.

4. The process of claim 1 wherein the glucoamylase has at least 97% sequence identity to the mature polypeptide of SEQ ID NO: 2.

5. The process of claim 1 wherein the glucoamylase has at least 98% sequence identity to the mature polypeptide of SEQ ID NO: 2.

6. The process of claim 1 wherein the glucoamylase has at least 99% sequence identity to the mature polypeptide of SEQ ID NO: 2.

7. The process of claim 1 wherein the glucoamylase has at least 90% sequence identity to the mature polypeptide of SEQ ID NO: 4.

8. The process of claim 1 wherein the glucoamylase has at least 95% sequence identity to the mature polypeptide of SEQ ID NO: 4.

9. The process of claim 1 wherein the glucoamylase has at least 97% sequence identity to the mature polypeptide of SEQ ID NO: 4.

10. The process of claim 1 wherein the glucoamylase has at least 98% sequence identity to the mature polypeptide of SEQ ID NO: 4.

11. The process of claim 1 wherein the glucoamylase has at least 99% sequence identity to the mature polypeptide of SEQ ID NO: 4.

12. The process of claim 1, wherein the fermenting organism is yeast.

13. A process of producing a fermentation product from starch-containing material comprising the steps of:
   (a) saccharifying starch-containing material at a temperature below the initial gelatinization temperature of said starch-containing material; and
   (c) fermenting with a fermenting organism;
wherein step (a) is carried out by contacting the starch-containing material with at least a glucoamylase having at least 85% sequence identity to the mature polypeptide of SEQ ID NO: 2 or SEQ ID NO: 4, and wherein the fermentation product is ethanol.

14. The process of claim 13 wherein the polypeptide has at least 90% sequence identity to the mature polypeptide of SEQ ID NO: 2.

15. The process of claim 13 wherein the polypeptide has at least 95% sequence identity to the mature polypeptide of SEQ ID NO: 2.

16. The process of claim 13 wherein the polypeptide has at least 97% sequence identity to the mature polypeptide of SEQ ID NO: 2.

17. The process of claim 13 wherein the polypeptide has at least 98% sequence identity to the mature polypeptide of SEQ ID NO: 2.

18. The process of claim 13 wherein the polypeptide has at least 99% sequence identity to the mature polypeptide of SEQ ID NO: 2.

19. The process of claim 13 wherein the polypeptide has at least 90% sequence identity to the mature polypeptide of SEQ ID NO: 4.

20. The process of claim 13 wherein the polypeptide has at least 95% sequence identity to the mature polypeptide of SEQ ID NO: 4.

21. The process of claim 13 wherein the polypeptide has at least 97% sequence identity to the mature polypeptide of SEQ ID NO: 4.

22. The process of claim 13 wherein the polypeptide has at least 98% sequence identity to the mature polypeptide of SEQ ID NO: 4.

23. The process of claim 13 wherein the polypeptide has at least 99% sequence identity to the mature polypeptide of SEQ ID NO: 4.

24. The process of claim 13, wherein the fermenting organism is yeast.

* * * * *

SEQUENCE LISTING

```
<160> NUMBER OF SEQ ID NOS: 8

<210> SEQ ID NO 1
<211> LENGTH: 1999
<212> TYPE: DNA
<213> ORGANISM: Chaetomium thermophilum

<400> SEQUENCE: 1
atgcctctct cgtcactcct tctcctgggc gcatgtgcct tccagtcggc ctttgcccgg      60
ccggccagcg ggaagcgcga tccccatatc ctcaagcgtg ccgtcgactc gtacatcgag     120
cgtgagacac ctatcgcctg aacaacctg ctgtgcaata tcggcggtcc gaatggctgc     180
cgggtcgctg gcgccgccac cggtgttgtt gttgccagcc cgtccaaggc aaatccggat     240
tgtgagttgt gtcattatta gtgaagaaaa gggggggggg gtggttgctc aggcagagat     300
gaaagatgct aatgctatct aatttttttt taaagacttt tacacctgga cccgtgatgc     360
agcccttgtc ttcaccagcg tgtcgactc cttctcacac acgtacaaca gcactctcca     420
gaccaacatc caaaattta tcgcctcgca ggccaagctg cagggcgtca ccaacccgtc     480
```

```
gggtggcctg tcggacggcg ccggcctggg cgagcccaag ttccacgtcg acctgacccg    540
cttcaacggc gaatggggtc gcccgcagcg cgacggcccg ccgctacgtg cgattgcgct    600
gatccgctat gccaagtggc tcatcaagaa cggctacgag tcgactgcta agaccgtcgt    660
gtggcccgtc atccgaaacg atttggccta caccgcccag tactggtccg agtccggctt    720
cgacctgtgg gaggaggtcg ccggcaactc cttcttcacc gtcgccagct cgcaccgtgc    780
gctcgtcgag ggtgcccatc tggctgctca gctcggcctc gagtgccgtg cctgcaccac    840
cgtcgccccg cacgtcctgt gctaccagca gaccttctgg aattccaatg gtaactacat    900
caactcgaac ctgaaccacg tcacaaccg cagcggcaag gacgccaact ctatcctcgt    960
ctccatccac aacttcgacc ccgccgtcgg ctgcgacgcg gcgaccttcc agccctgcag   1020
tgatcgcgcc ttggccaacc acaaggccta cgtcgactcc ttccgctccg tctactccat   1080
caacagaggc atctcccagg gccgccgt cgccgtcggc cgctacagcg aggacgtcta   1140
ctacaatggc aacccgtggt acctggccgt ctttgccgcc gccgagcagc tctacgacgc   1200
cctctacgtc tggaagaagc agggttccat caccatcacc tctgtctccc ttcccttctt   1260
ccgggacctc ctgcccctcca tcaccacggg cacctacaac tctcgctcct ccacttccca   1320
gtccatcatc gacgccgtcc agacctacgc cgatgacttc atggccatcg ccgagaagta   1380
tactccctcg gacggctccc tgaccgagca atttgaccgc aacacgggcg cacccatcgc   1440
cgcgccccac ctgacttggt cctacgccgc cttcatcacc gccgccgagc ggcgcgcggg   1500
catcgtcccc gagggctggt ccgcgcagta cggcaacacc gtccccctcgt cctgctcgcg   1560
cacccgtgcag gtgccggca cttacgcgac cgcgaccgcg acctccttcc cggccaaaca   1620
gaccccaaa tccggcgccg ccccggctcc ctcgcctttc ccgaccacct gcaagaacgc   1680
gaacgaggtg tacgtcacct tcaccaccg cgcccgagacg cagtggggcc agacggtcaa   1740
gttggtgggc tcgatccccg agctgggcag ctggaacacg aacaaggcga tcccgctgag   1800
cgcggtcggc tacacgggcg atagcaaccc gctctggagc attactgtgc cactgaagaa   1860
ggggacgagc tttgagtaca agttcatcaa ggtcaactcg aatgggtcgg tgcagtggga   1920
gagcgatccg aataggagct ttaccccgac cgcgagcggg aactgcccga gtcagaccca   1980
ggaggcttcg tggcgttag                                                1999

<210> SEQ ID NO 2
<211> LENGTH: 634
<212> TYPE: PRT
<213> ORGANISM: Chaetomium thermophilum

<400> SEQUENCE: 2

Met Pro Leu Ser Ser Leu Leu Leu Gly Ala Cys Ala Phe Gln Ser
1               5                   10                  15

Ala Phe Ala Arg Pro Ala Ser Gly Lys Arg Asp Pro His Ile Leu Lys
            20                  25                  30

Arg Ala Val Asp Ser Tyr Ile Glu Arg Glu Thr Pro Ile Ala Trp Asn
        35                  40                  45

Asn Leu Leu Cys Asn Ile Gly Gly Pro Asn Gly Cys Arg Val Ala Gly
    50                  55                  60

Ala Ala Thr Gly Val Val Ala Ser Pro Lys Ala Asn Pro Asp
65                  70                  75                  80

Tyr Phe Tyr Thr Trp Thr Arg Asp Ala Ala Leu Val Phe Thr Ser Val
                85                  90                  95

Val Asp Ser Phe Ser His Thr Tyr Asn Ser Thr Leu Gln Thr Asn Ile
```

```
                    100                 105                 110
        Gln Asn Phe Ile Ala Ser Gln Ala Lys Leu Gln Gly Val Thr Asn Pro
                        115                 120                 125
        Ser Gly Gly Leu Ser Asp Gly Ala Gly Leu Gly Glu Pro Lys Phe His
                130                 135                 140
        Val Asp Leu Thr Arg Phe Asn Gly Glu Trp Gly Arg Pro Gln Arg Asp
        145                 150                 155                 160
        Gly Pro Pro Leu Arg Ala Ile Ala Leu Ile Arg Tyr Ala Lys Trp Leu
                        165                 170                 175
        Ile Lys Asn Gly Tyr Glu Ser Thr Ala Lys Thr Val Val Trp Pro Val
                        180                 185                 190
        Ile Gln Asn Asp Leu Ala Tyr Thr Ala Gln Tyr Trp Ser Glu Ser Gly
                        195                 200                 205
        Phe Asp Leu Trp Glu Glu Val Ala Gly Asn Ser Phe Phe Thr Val Ala
                        210                 215                 220
        Ser Ser His Arg Ala Leu Val Glu Gly Ala His Leu Ala Ala Gln Leu
        225                 230                 235                 240
        Gly Leu Glu Cys Arg Ala Cys Thr Thr Val Ala Pro His Val Leu Cys
                            245                 250                 255
        Tyr Gln Gln Thr Phe Trp Asn Ser Asn Gly Asn Tyr Ile Asn Ser Asn
                        260                 265                 270
        Leu Asn His Gly His Asn Arg Ser Gly Lys Asp Ala Asn Ser Ile Leu
                        275                 280                 285
        Val Ser Ile His Asn Phe Asp Pro Ala Val Gly Cys Asp Ala Ala Thr
                290                 295                 300
        Phe Gln Pro Cys Ser Asp Arg Ala Leu Ala Asn His Lys Ala Tyr Val
        305                 310                 315                 320
        Asp Ser Phe Arg Ser Val Tyr Ser Ile Asn Arg Gly Ile Ser Gln Gly
                        325                 330                 335
        Arg Ala Val Ala Val Gly Arg Tyr Ser Glu Asp Val Tyr Tyr Asn Gly
                        340                 345                 350
        Asn Pro Trp Tyr Leu Ala Val Phe Ala Ala Glu Gln Leu Tyr Asp
                        355                 360                 365
        Ala Leu Tyr Val Trp Lys Lys Gln Gly Ser Ile Thr Ile Thr Ser Val
                        370                 375                 380
        Ser Leu Pro Phe Phe Arg Asp Leu Leu Pro Ser Ile Thr Thr Gly Thr
        385                 390                 395                 400
        Tyr Asn Ser Arg Ser Ser Thr Phe Gln Ser Ile Ile Asp Ala Val Gln
                        405                 410                 415
        Thr Tyr Ala Asp Asp Phe Met Ala Ile Ala Glu Lys Tyr Thr Pro Ser
                        420                 425                 430
        Asp Gly Ser Leu Thr Glu Gln Phe Asp Arg Asn Thr Gly Ala Pro Ile
                        435                 440                 445
        Ala Ala Pro His Leu Thr Trp Ser Tyr Ala Ala Phe Ile Thr Ala Ala
                        450                 455                 460
        Glu Arg Arg Ala Gly Ile Val Pro Glu Gly Trp Ser Ala Gln Tyr Gly
        465                 470                 475                 480
        Asn Thr Val Pro Ser Ser Cys Ser Arg Thr Leu Gln Val Ala Gly Thr
                            485                 490                 495
        Tyr Ala Thr Ala Thr Ala Thr Ser Phe Pro Ala Lys Gln Thr Pro Lys
                        500                 505                 510
        Ser Gly Ala Ala Pro Ala Pro Ser Pro Phe Pro Thr Thr Cys Lys Asn
                        515                 520                 525
```

```
Ala Asn Glu Val Tyr Val Thr Phe His His Arg Ala Gln Thr Gln Trp
            530                 535                 540

Gly Gln Thr Val Lys Leu Val Gly Ser Ile Pro Glu Leu Gly Ser Trp
545                 550                 555                 560

Asn Thr Asn Lys Ala Ile Pro Leu Ser Ala Val Gly Tyr Thr Gly Asp
                565                 570                 575

Ser Asn Pro Leu Trp Ser Ile Thr Val Pro Leu Lys Lys Gly Thr Ser
            580                 585                 590

Phe Glu Tyr Lys Phe Ile Lys Val Asn Ser Asn Gly Ser Val Gln Trp
595                 600                 605

Glu Ser Asp Pro Asn Arg Ser Phe Thr Pro Thr Ala Ser Gly Asn Cys
            610                 615                 620

Pro Ser Gln Thr Gln Glu Ala Ser Trp Arg
625                 630
```

<210> SEQ ID NO 3
<211> LENGTH: 2064
<212> TYPE: DNA
<213> ORGANISM: Chaetomium thermophilum

<400> SEQUENCE: 3

```
atgccattga ttaaaacact ggcattaaca ggcctactag cttctcaggg gctggcagga    60
gctatccctc agactttgtc ccttgaaaaa tggatcaaga ccgtaagct gctctcacat   120
acggatatgt caagaataga actatctaat gtctgttaga gcgagcaatt gccctggaag   180
gagtcctcga caatattggc gccaatggta ccaaggttgc tggagcagga cgcggtctcg   240
tcatcgccag tccatcaaag tcaaatcctg actgtatgtc aattcgacta cttgaagttt   300
cacgaaccct ctaacacaca cacacacaca gacttctaca cttggactcg cgactctgcc   360
ctcactttcc ggaccatcat cgacgacttc ctctttggaa caaggccct tcagccacac   420
atcgagaact acatctactc ccaggctatc ctccaaacgg tcagcaaccc atcaggctca   480
cttctcccca acggtgctgg tctcggcgag cccaagttca acgctgatgg gtcgagatac   540
aatgggaact ggggtcggcc tcagagagac ggtcctccat tgagggctat ctctctcatc   600
cagtatagca actatcttat ctcccaagag cagaaggaga gggttaagag ggagatctgg   660
ccaatcatta gcaatgatct gaactatgtt gggcagtact ggtgggtgtc tctgaacttg   720
atcaagccaa gaagccaaag ctaaccgctg agcaggaacg ccacaacctt tgacctttgg   780
gaggaagttt ctggcgcttc cttcttcacc acccaatccc aataccgcgc cctcatcgag   840
ggctctaccc tcgctaagtc cctcaatctc tcttgcccag cttgctcgca agcccctcag   900
atcctctgcc tgcttaattc gtactggaac ggcgcctact acacggcaaa cttcatcacc   960
tccacggccg acagccaac tggccgggta ggcatagatg caaacacgat ccttgggccg  1020
atcatggcct ttgaccccaa tgcttcatgc aacagtccta cgctacagcc atgccatcca  1080
aaaagcctgg ccaacttcaa agctgtcgtt gacaccttcc gcactctcta tcccattaac  1140
gaaggcatcc ctgtcggtaa aggcattgct ttaggccgct accccgaaga tacctacttc  1200
ggcggcaacc cctggtacct aatcgtccac ggggccgcag aatttctcta cgacgtcgcc  1260
ctgtcctggt ctcgccaggg gcagataacc attacttcaa cctcacttcc ctttttaag   1320
gacctctatc cctctgccaa aatcgggaca tattcgaagt ctcatccaac ttaccatgcc  1380
ttggcaaaag ccgtgcacgc ctacgccgac tccttcatcg aggtctccaa gaaatatact  1440
ccctccaacg gcatgcaagc agagcaattc ctccgcattt ccccggac tccaacctcc   1500
```

```
gccgcaaacc tgacctggtc cttcgcctcc ttcatttcca tgactcaccg gcgcgatgga   1560
catcttcctg caagctgggt cccgactggt cggaatgccc ctgttttgcc ccaaatttgt   1620
accccaagcg acggctcctt cattggcacc ttcgctcccg caaccgaggc cggcgcaccc   1680
aacatcaaaa tcccctgcct cacaactgtc cgcttcatgg tcgacgcacc gacttactac   1740
ggcgagaacg tctttattac gggcagcacg cccacactag ggaactggga cgtgtctaaa   1800
gcttatccct tactcagcag caattatact gctgaacgcc cgctctggtg gcagacgtc    1860 ctgctggagt ttgaggaggg ctttaagggg ggcgaggtga ggtataagta tgctagacag   1920
caggattgtg gcaggattg gattgttgag caggacgaga gggttgtgac tgtgccgggg    1980
tgtaaggttg ggggttcggg ggttgttgat gtggttgtgg aggaggtgtt taacggggat   2040
gggggcactc ccggcggttg ctaa                                         2064
```

<210> SEQ ID NO 4
<211> LENGTH: 631
<212> TYPE: PRT
<213> ORGANISM: Chaetomium thermophilum

<400> SEQUENCE: 4

```
Met Pro Leu Ile Lys Thr Leu Ala Leu Thr Gly Leu Leu Ala Ser Gln
1               5                   10                  15

Gly Leu Ala Gly Ala Ile Pro Gln Thr Leu Ser Leu Glu Lys Trp Ile
            20                  25                  30

Lys Thr Glu Arg Ala Ile Ala Leu Glu Gly Val Leu Asp Asn Ile Gly
        35                  40                  45

Ala Asn Gly Thr Lys Val Ala Gly Ala Gly Arg Gly Leu Val Ile Ala
    50                  55                  60

Ser Pro Ser Lys Ser Asn Pro Asp Tyr Phe Tyr Thr Trp Thr Arg Asp
65                  70                  75                  80

Ser Ala Leu Thr Phe Arg Thr Ile Ile Asp Asp Phe Leu Phe Gly Asn
                85                  90                  95

Lys Ala Leu Gln Pro His Ile Glu Asn Tyr Ile Tyr Ser Gln Ala Ile
            100                 105                 110

Leu Gln Thr Val Ser Asn Pro Ser Gly Ser Leu Leu Pro Asn Gly Ala
        115                 120                 125

Gly Leu Gly Glu Pro Lys Phe Asn Ala Asp Gly Ser Arg Tyr Asn Gly
    130                 135                 140

Asn Trp Gly Arg Pro Gln Arg Asp Gly Pro Leu Arg Ala Ile Ser
145                 150                 155                 160

Leu Ile Gln Tyr Ser Asn Tyr Leu Ile Ser Gln Glu Gln Lys Glu Arg
                165                 170                 175

Val Lys Arg Glu Ile Trp Pro Ile Ile Ser Asn Asp Leu Asn Tyr Val
            180                 185                 190

Gly Gln Tyr Trp Asn Ala Thr Thr Phe Asp Leu Trp Glu Glu Val Ser
        195                 200                 205

Gly Ala Ser Phe Phe Thr Thr Gln Ser Gln Tyr Arg Ala Leu Ile Glu
    210                 215                 220

Gly Ser Thr Leu Ala Lys Ser Leu Asn Leu Ser Cys Pro Ala Cys Ser
225                 230                 235                 240

Gln Ala Pro Gln Ile Leu Cys Leu Leu Asn Ser Tyr Trp Asn Gly Ala
                245                 250                 255

Tyr Tyr Thr Ala Asn Phe Ile Thr Ser Thr Ala Gly Gln Pro Thr Gly
            260                 265                 270
```

Arg Val Gly Ile Asp Ala Asn Thr Ile Leu Gly Pro Ile Met Ala Phe
               275                 280                 285

Asp Pro Asn Ala Ser Cys Asn Ser Pro Thr Leu Gln Pro Cys His Pro
       290                 295                 300

Lys Ser Leu Ala Asn Phe Lys Ala Val Val Asp Thr Phe Arg Thr Leu
305                 310                 315                 320

Tyr Pro Ile Asn Glu Gly Ile Pro Val Gly Lys Gly Ile Ala Leu Gly
                   325                 330                 335

Arg Tyr Pro Glu Asp Thr Tyr Phe Gly Gly Asn Pro Trp Tyr Leu Ile
               340                 345                 350

Val His Gly Ala Ala Glu Phe Leu Tyr Asp Val Ala Leu Ser Trp Ser
               355                 360                 365

Arg Gln Gly Gln Ile Thr Ile Thr Ser Thr Ser Leu Pro Phe Phe Lys
       370                 375                 380

Asp Leu Tyr Pro Ser Ala Lys Ile Gly Thr Tyr Ser Lys Ser His Pro
385                 390                 395                 400

Thr Tyr His Ala Leu Ala Lys Ala Val His Ala Tyr Ala Asp Ser Phe
                   405                 410                 415

Ile Glu Val Ser Lys Lys Tyr Thr Pro Ser Asn Gly Met Gln Ala Glu
               420                 425                 430

Gln Phe Leu Arg Ile Ser Pro Gly Thr Pro Thr Ser Ala Ala Asn Leu
       435                 440                 445

Thr Trp Ser Phe Ala Ser Phe Ile Ser Met Thr His Arg Arg Asp Gly
450                 455                 460

His Leu Pro Ala Ser Trp Val Pro Thr Gly Arg Asn Ala Pro Val Leu
465                 470                 475                 480

Pro Gln Ile Cys Thr Pro Ser Asp Gly Ser Phe Ile Gly Thr Phe Ala
                   485                 490                 495

Pro Ala Thr Glu Ala Gly Ala Pro Asn Ile Lys Ile Pro Cys Leu Thr
               500                 505                 510

Thr Val Arg Phe Met Val Asp Ala Pro Thr Tyr Tyr Gly Glu Asn Val
       515                 520                 525

Phe Ile Thr Gly Ser Thr Pro Thr Leu Gly Asn Trp Asp Val Ser Lys
530                 535                 540

Ala Tyr Pro Leu Leu Ser Ser Asn Tyr Thr Ala Glu Arg Pro Leu Trp
545                 550                 555                 560

Trp Ala Asp Val Leu Leu Glu Phe Glu Glu Gly Phe Lys Gly Gly Glu
                   565                 570                 575

Val Arg Tyr Lys Tyr Ala Arg Gln Gln Asp Cys Gly Gln Asp Trp Ile
               580                 585                 590

Val Glu Gln Asp Glu Arg Val Val Thr Val Pro Gly Cys Lys Val Gly
       595                 600                 605

Gly Ser Gly Val Val Asp Val Val Glu Glu Val Phe Asn Gly Asp
610                 615                 620

Gly Gly Thr Pro Gly Gly Cys
625                 630

<210> SEQ ID NO 5
<211> LENGTH: 36
<212> TYPE: DNA
<213> ORGANISM: Artificial
<220> FEATURE:
<223> OTHER INFORMATION: PCR primer

<400> SEQUENCE: 5

```
acacaactgg ggatcaccat gcctctctcg tcactc                              36

<210> SEQ ID NO 6
<211> LENGTH: 40
<212> TYPE: DNA
<213> ORGANISM: Artificial
<220> FEATURE:
<223> OTHER INFORMATION: PCR primer

<400> SEQUENCE: 6
ccctctagat ctcgagaaat ctaacgccac gaagcctcct                          40

<210> SEQ ID NO 7
<211> LENGTH: 48
<212> TYPE: DNA
<213> ORGANISM: Artificial
<220> FEATURE:
<223> OTHER INFORMATION: PCR primer

<400> SEQUENCE: 7
acacaactgg ggatccacca tgccattgat taaaacactg gcattaac                 48

<210> SEQ ID NO 8
<211> LENGTH: 41
<212> TYPE: DNA
<213> ORGANISM: Artificial
<220> FEATURE:
<223> OTHER INFORMATION: PCR primer

<400> SEQUENCE: 8
gtcaccctct agatctcgag actcggccaa tctcggcttt a                        41
```